(12) United States Patent
Robinson et al.

(10) Patent No.: US 8,771,745 B2
(45) Date of Patent: Jul. 8, 2014

(54) PROSTAGLANDIN AND PROSTAMIDE DRUG DELIVERY SYSTEMS AND INTRAOCULAR THERAPEUTIC USES THEREOF

(75) Inventors: Michael R. Robinson, Irvine, CA (US); Hui Liu, Irvine, CA (US); Patrick M. Hughes, Aliso Viejo, CA (US); Lon T. Spada, Walnut, CA (US); Alazar N. Ghebremeskel, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/596,904

(22) Filed: Aug. 28, 2012

(65) Prior Publication Data

US 2013/0017268 A1  Jan. 17, 2013

Related U.S. Application Data

(62) Division of application No. 12/259,153, filed on Oct. 27, 2008, now abandoned.

(30) Foreign Application Priority Data

Oct. 23, 2009  (WO) .......................... PCT200961798

(51) Int. Cl.
*A61K 9/14*  (2006.01)
*A61K 9/00*  (2006.01)

(52) U.S. Cl.
CPC .................................... *A61K 9/0048* (2013.01)
USPC ......................................................... 424/489

(58) Field of Classification Search
CPC .................................................... A61K 9/0048
USPC ......................................................... 424/489
See application file for complete search history.

(56) References Cited

U.S. PATENT DOCUMENTS

| | | |
|---|---|---|
| 4,327,725 A | 5/1982 | Cortese |
| 4,474,451 A | 10/1984 | Mizokami |
| 4,851,513 A | 7/1989 | Devore et al. |
| 5,166,331 A | 11/1992 | Della Valle |
| 5,824,658 A | 10/1998 | Falk et al. |
| 5,869,079 A | 2/1999 | Wong |
| 6,831,172 B1 | 12/2004 | Barbucci et al. |
| 7,586,057 B2 | 9/2009 | Sisson et al. |
| 7,589,057 B2 | 9/2009 | Chang et al. |
| 7,799,336 B2 | 9/2010 | Hughes et al. |
| 7,993,634 B2 | 8/2011 | Hughes et al. |
| 2002/0035264 A1 | 3/2002 | Kararli et al. |
| 2004/0013643 A1 | 1/2004 | Mach |
| 2004/0029970 A1 | 2/2004 | Rask-Andersen et al. |
| 2004/0175410 A1 | 9/2004 | Ashton et al. |

(Continued)

FOREIGN PATENT DOCUMENTS

WO  WO94/14117  7/1994

OTHER PUBLICATIONS

U.S. Appl. No. 10/837,260, filed Apr. 30, 2004.
U.S. Appl. No. 10/966,764, filed Oct. 14, 2004.

(Continued)

*Primary Examiner* — Benjamin Packard
(74) *Attorney, Agent, or Firm* — Laura L. Wine; Joel B. German; Debra D. Condino

(57) ABSTRACT

Biocompatible, bioerodible implants and microspheres include latanoprost and a biodegradable polymer effective, when placed intraocular (such as into the subtenon space) to treat glaucoma.

1 Claim, 5 Drawing Sheets
(5 of 5 Drawing Sheet(s) Filed in Color)

Formulation Summary

| Lot number | Polymer | 1st day release | process % Yield | drug load % | PS before freeze drying, um | | | PS after freeze |
|---|---|---|---|---|---|---|---|---|
| | | | | | d10 | d90 | Mean | Mean |
| MP-2 | 203H | | 84% | 10.4% | | | | |
| MP-3 | 203H | | 77% | 9.8% | | | | |
| MP-4 | 203H | | 82% | 10.3% | | | | |
| MP-5 | 203H | | 78% | 13.5% | | | | |
| MP-6 | RG502H | | 77% | 13.3% | | | | |
| MP-7 | RG502 | | 71% | 10.7% | | | | |
| MP-8 | R203S | | 83% | 12.2% | | | | |
| MP-9 | R208 | | 77% | 8.5% | | | | |
| MP-10 | RG752S | | 85% | 11.1% | | | | |
| MP-11 | RG755 | | 84% | 11.9% | | | | |
| MP-12 | R202H | | 79% | 11.6% | | | | |
| MP-13 | RG503H | | 76% | 12.1% | | | | |
| MP-14 | RG755S | | 67% | 10.6% | | | | |
| MP-15 | 3:1 203H:502H | | 76% | 10.2% | | | | |
| MP-16 | 1:1 203H:502H | | 78% | 9.1% | | | | |
| MP-17 | 1:3 203H:502H | | 76% | 8.0% | | | | |

(56) References Cited

U.S. PATENT DOCUMENTS

| | | | |
|---|---|---|---|
| 2005/0101582 | A1 | 5/2005 | Lyons et al. |
| 2005/0181017 | A1 | 8/2005 | Hughes et al. |
| 2005/0244464 | A1 | 11/2005 | Hughes |
| 2005/0244469 | A1 | 11/2005 | Whitcup et al. |
| 2005/0244477 | A1 | 11/2005 | Hughes et al. |
| 2006/0099256 | A1 | 5/2006 | Price et al. |
| 2006/0141049 | A1 | 6/2006 | Lyons et al. |
| 2006/0182781 | A1 | 8/2006 | Hughes |
| 2006/0210604 | A1 | 9/2006 | Dadey et al. |
| 2006/0246145 | A1 | 11/2006 | Chang et al. |
| 2007/0099256 | A1 | 5/2007 | Sundararajan et al. |
| 2007/0224246 | A1 | 9/2007 | Hughes et al. |
| 2007/0224278 | A1 | 9/2007 | Lyons et al. |
| 2008/0033351 | A1 | 2/2008 | Trogden et al. |
| 2008/0131484 | A1 | 6/2008 | Robinson et al. |
| 2008/0145403 | A1 | 6/2008 | Spada et al. |
| 2008/0181930 | A1 | 7/2008 | Rodstrom |
| 2009/0082321 | A1 | 3/2009 | Edelman et al. |
| 2009/0148527 | A1 | 6/2009 | Robinson et al. |
| 2009/0149435 | A1 | 6/2009 | Wang et al. |
| 2010/0074957 | A1 | 3/2010 | Robinson et al. |
| 2010/0124565 | A1 | 5/2010 | Spada et al. |
| 2010/0247606 | A1 | 9/2010 | Robinson et al. |

OTHER PUBLICATIONS

U.S. Appl. No. 11/039,192, filed Jan. 19, 2005.
U.S. Appl. No. 11/303,462, filed Dec. 15, 2005.
U.S. Appl. No. 11/368,845, filed Mar. 6, 2006.
U.S. Appl. No. 11/612,928, filed Dec. 19, 2006.
U.S. Appl. No. 11/741,366, filed Apr. 27, 2007.
U.S. Appl. No. 11/859,627, filed Sep. 21, 2007.
U.S. Appl. No. 11/952,927, filed Dec. 7, 2007.
Burk, Robert. "Bimatoprost, a Novel Efficacious Ocular Hypotensive Drug Now Recognized as a Member of a New Class of Agents Called Prostamides." Drug Development Research 68(2007): pp. 147-155.
Cantor, Louis. "Bimatoprost: a member of a new class of agents, the prostamides, for glaucoma management." Exo ODin Invest Druas 10(4)(2001): pp. 721-731.
Heller, Biodegradable Polymers in Controlled Drug Delivery (1987) CRC Critical Reviews in Therapeutic DruQ Carrier Systems, vol. 1, Issue 1 :39-90.
United States Pharmacopeia (USP 23); National Formulary (NF 18),1995, pp. 1790-1798.
Woodward, David. "Prostamides (prostaglandin-ethanolamides) and their pharmacology." British Journal of Pharmacoloav 153(3)(2008): pp. 410-419.
Herrero-Vanrell et al. (2001) "Biodegradable microspheres for vitreoretinal drug delivery" *Adv. Drug Delivery Reviews* 52:5-16.
Ludwig et al, "The use of mucoadhesive polymers in ocular drug delivery", Advanced Drug Delivery Reviews, vol. 57, Issue 11, (2005) 1595-1639.
"Subconjunctival Injection", Chapter 97, pp. 432-435, in Atlas of Primary Eyecare Procedures, $2^{nd}$ Ed., Casser, Fingeret, and Woodcome, Copyright 1997 by Appleton & Lange.
U.S. Appl. No. 12/626,408, filed Nov. 25, 2009.
Wine et al. (1964) "The ocular uptake of subconjunctivally injected $C^{14}$ hydrocortisone" *Am. J. Ophthalmol.* 58:362-6.

Formulation Summary

| Lot number | Polymer | 1st day release | process % Yield | drug load % | PS before freeze drying, um d10 | d90 | Mean | PS after freeze Mean |
|---|---|---|---|---|---|---|---|---|
| MP-2 | 203H | 6.0% | 84% | 10.4% | 16.5 | 65.4 | 35.9 | |
| MP-3 | 203H | 9.6% | 77% | 9.8% | 14.5 | 55.5 | 30.3 | |
| MP-4 | 203H | 9.5% | 82% | 10.3% | 17.0 | 67.2 | 36.6 | |
| MP-5 | 203H | 7.0% | 78% | 13.5% | 15.4 | 59.2 | 31.9 | |
| MP-6 | RG502H | 8.7% | 77% | 13.3% | 16.5 | 57.9 | 32.2 | 32.8 |
| MP-7 | RG502 | 6.9% | 71% | 10.7% | 15.3 | 52.4 | 29.4 | 30.3 |
| MP-8 | R203S | 10.6% | 83% | 12.2% | 15.8 | 64.5 | 34.7 | 35.2 |
| MP-9 | R208 | 16.0% | 77% | 8.5% | 12.5 | 48.4 | 26.5 | 27.6 |
| MP-10 | RG752S | 6.8% | 85% | 11.1% | 12.9 | 60 | 27.1 | 26.9 |
| MP-11 | RG755 | 3.2% | 84% | 11.9% | 17.4 | 66.3 | 35.6 | 36.3 |
| MP-12 | R202H | 22.4% | 79% | 11.6% | 13.7 | 59.9 | 30.9 | |
| MP-13 | RG503H | 5.5% | 76% | 12.1% | 21.8 | 69.5 | 40.4 | |
| MP-14 | RG755S | 6.8% | 67% | 10.6% | 13.9 | 102 | 52.2 | |
| MP-15 | 3:1 203H:502H | 4.6% | 76% | 10.2% | 18.5 | 63.2 | 35.7 | |
| MP-16 | 1:1 203H:502H | 44.8% | 78% | 9.1% | 14.9 | 35.8 | 23.3 | |
| MP-17 | 1:3 203H:502H | 60.0% | 76% | 8.0% | 10.4 | 29.3 | 17.7 | |

FIG. 1

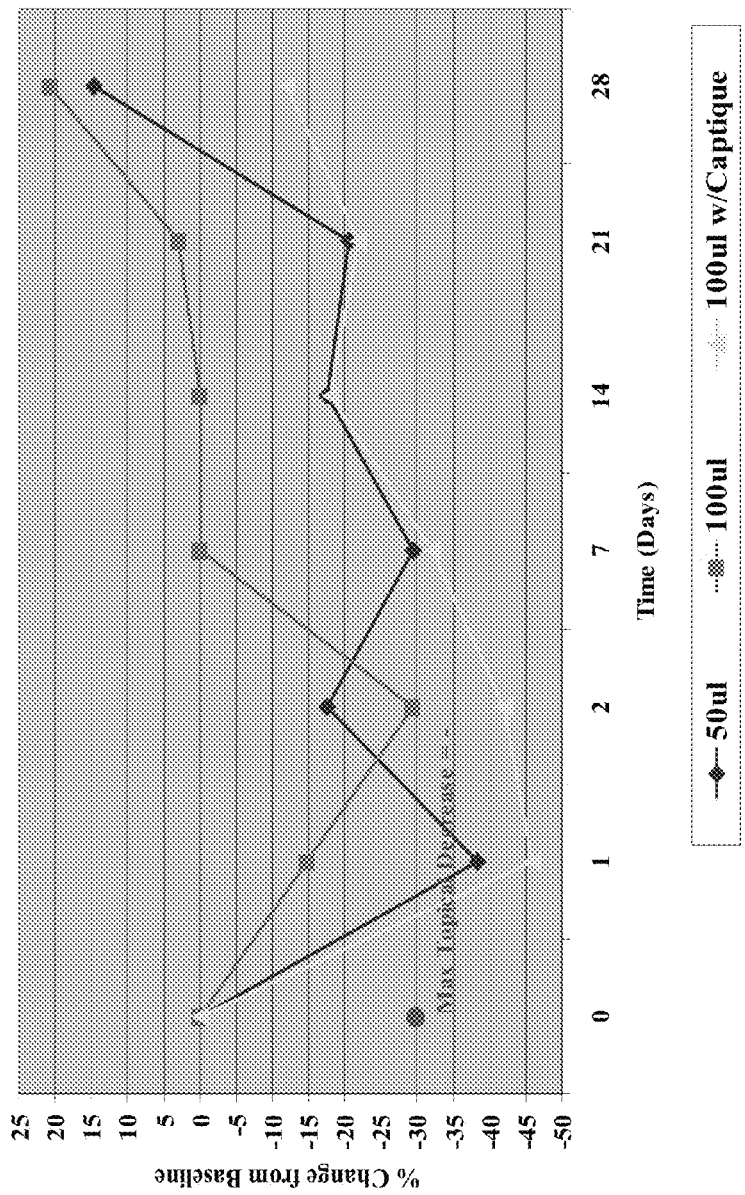

PROSTAGLANDIN AND PROSTAMIDE DRUG DELIVERY SYSTEMS AND INTRAOCULAR THERAPEUTIC USES THEREOF

CROSS-REFERENCE TO RELATED APPLICATIONS

This application is a divisional of U.S. application Ser. No. 12/259,153, filed Oct. 27, 2008. The entire disclosure of U.S. application Ser. No. 12/259,153 is incorporated herein by reference.

BACKGROUND

The present invention relates to prostaglandin and/or prostamide (as well as to esters, salts and derivatives thereof) drug delivery systems for intraocular use. Prostaglandins are a class of pharmacologically active hormone like substances made in various mammalian tissues, which are derived from arachidonic acid, and mediate a wide range of physiological functions including blood pressure, smooth muscle contraction and inflammation. Examples of prostaglandins are prostaglandin $E_1$ (alprostadil), prostaglandin $E_2$ (dinoprostone), latanoprost and travoprost. Latanoprost and travoprost are actually prostaglandin prodrugs (i.e. 1-isopropyl esters of a prostaglandin) however, they are referred to as prostaglandins because they act on the prostaglandin F receptor, after being hydrolyzed to the 1-carboxylic acid. A prostamide (also called a prostaglandin-ethanolamide) is a prostaglandin analogue, which is pharmacologically unique from a prostaglandin (i.e. because prostamides act on a different cell receptor [the prostamide receptor] than do prostaglandins), and is a neutral lipid formed a as product of cyclo-oxygenase-2 ("COX-2") enzyme oxygenation of an endocannabinoid (such as anandamide). Additionally, prostamides do not hydrolyze in-situ to the 1-carboxylic acid. Examples of prostamides are bimatoprost (the synthetically made ethyl amide of 17-phenyl prostaglandin $F_{2\alpha}$) and prostamide $F_{2\alpha}$. The drug delivery systems of our invention can be a drug containing implant or implants or a plurality of drug containing microspheres (synonymously "microparticles"). The drug delivery system can be used therapeutically to treat an ocular disease or condition.

Glaucoma is a disease of the eye characterized by increased intraocular pressure. Glaucoma can be classified as primary or secondary. Primary glaucoma in adults (congenital glaucoma) may be either open-angle or acute or chronic angle-closure. Secondary glaucoma results from pre-existing ocular diseases such as uveitis, intraocular tumor or an enlarged cataract.

Certain prostaglandins and their analogs and derivatives, such as the $PGF_{2\alpha}$ derivative (sometimes referred to as prostaglandin F2α analogue) latanoprost, sold under the trademark Xalatan®, have been used to treat ocular hypertension and glaucoma. Unfortunately, when topically administered (i.e. as eye drops) latanoprost can have the undesirable side effects of changing the patient's eye color (by increasing iris brown pigment) and causing hyperemia (eye redness or inflammation). Hence, topical administration of latanoprost can be undesirable for both cosmetic and patient comfort reasons.

Intraocular prostaglandin and prostamide implant and microspheres are disclosed by U.S. patent application Ser. Nos. 11/368,845; 11/303,462; and; 10/837,260.

Thus it would be advantageous to provide sustained release latanoprost containing implants and microspheres for intraocular (as opposed to topical) therapeutic use to treat glaucoma, with few or no negative side effects, such as no or substantially no change to iris pigmentation or hyperemia. Such implants or microspheres by releasing the drug over a multiday period can provide an alternative to daily topical administration of latanoprost eyedrops to lower intraocular pressure ("IOP"), thereby treating glaucoma with increased patient compliance (since daily dosing is not required) using a sustained release formulation (latanoprost containing microspheres).

SUMMARY

The present invention provides a novel pharmaceutical composition and glaucoma treatment methods. The composition is in the form of an implant or microspheres which advantageously provide for extended release times of one or more therapeutic agents which is a prostaglandin or a prostamide, such as latanoprost. The implants or the microspheres can release the drug over a relatively long period of time, for example, for at least about one week or for example for between about two months and about six months, after intraocular (i.e. intrascleral) administration of latanoprost containing implant or microspheres. Such extended release times facilitate obtaining successful treatment results. In addition, administering such implant or microparticles sub-conjunctivally (i.e. sub-tenon) can reduce the occurrence and/or severity of at least one side effect, for example, iris color change and/or hyperemia, relative to administering an identical amount of the latanoprost to the eye in the form of a topical composition.

An embodiment of our invention is a pharmaceutical composition for intraocular use to treat an ocular condition. The composition can comprise a plurality of microspheres made of a bioerodible polymer, and a therapeutic agent selected from the group consisting of latanoprost, bimatoprost and travoprost and their salts, esters and derivatives, contained by the microspheres. The microspheres can comprise from about 1% to about 99% by weight of the polymer and the polymer can be a PLGA and/or PLA. Additionally, the microspheres can have an average greatest dimension in a range of from about 5 microns to about 1 mm, for example the microspheres can have a mean diameter between about 15 microns and about 55 microns and the therapeutic agent can comprise from about 0.1% to about 90% by weight of the microspheres, such as between about 8 to 15 weight % latanoprost.

In another embodiment of our invention the composition can include a high viscosity hyaluronic acid and the ocular condition treated can be glaucoma.

A detailed embodiment of our invention is a pharmaceutical composition for intraocular use to treat glaucoma comprising a plurality of microspheres made from a PLGA and/or PLA, latanoprost contained by the microspheres, and a high viscosity hyaluronic acid.

Another embodiment of our invention is a pharmaceutical composition for intraocular use to treat glaucoma, the composition comprising a sustained release implant made from a PLGA polymer, a PLA polymer, and a PEG co-solvent, and; latanoprost contained by the implant, wherein the implant comprises about 30 weight percent latanoprost and the implant can release the latanoprost over a period of time of at least 20, 30, 40, 50, 60, 70 or up to 180 days.

Another embodiment of our invention is a method of treating glaucoma, the method comprising intraocular administration to a patient with glaucoma of a pharmaceutical composition comprising the implant set forth above or a plurality of microspheres made from a PLGA and/or PLA; latanoprost contained by the microspheres, and a high viscosity hyaluronic acid (HA), thereby treating the glaucoma. Preferably, the HA is used with the plurality of microspheres formulation but not with the single implant administered. The microspheres can release the latanoprost for at least about one week after the administration step. The intraocular administration step can be carried out by injection into the sub-tenon space, such as into the anterior sub-tenon space and the pharmaceutical composition treats glaucoma by reducing baseline intraocular pressure by up to 20%, 30%, 40% or up to 45%.

Within the scope of our invention is a formulation of latanoprost containing microspheres which can release therapeutically effective amounts of the latanoprost from the microspheres in vivo (i.e. upon intraocular administration of the microspheres) over a period of time from about 1 week to about six months, including for a period of time of two, three, four, five or six months.

Another embodiment of our invention is a method of treating glaucoma, the method comprising anterior sub-tenon administration to a patient with glaucoma of a pharmaceutical composition comprising a plurality of microspheres made from a PLGA and/or PLA; latanoprost contained by the microspheres, wherein the microspheres release the latanoprost for at least about one week (such as for about two months) after the administration step, and; a high viscosity hyaluronic acid, thereby treating the glaucoma by reducing baseline intraocular pressure by up to about 45%.

Additional aspects and advantages of the present invention are set forth in the following description and claims, particularly when considered in conjunction with the accompanying drawings.

DRAWINGS

The patent or application file contains at least one drawing executed in color. Copies of this patent application publication with color drawing(s) will be provided by the Office upon request and payment of the necessary fee.

FIG. 1 is a table showing characteristics of sixteen (MP-2 to MP-17) different batches of latanoprost containing microspheres made by the method of Example 1, showing the bioerodible polymer(s) used, the amount of latanoprost released form each type of microsphere after one day in vitro, the weight percent of latanoprost loaded in the microspheres and, the diameter of the latanoprost containing microspheres made before and after lyophilization.

FIG. 3 is a graph showing in vivo (in dogs) percent change from baseline IOP over a 28 day period after sub-tenon injection of the FIG. 1 MP-5 microspheres in three different formulations (a 50 ul concentration, a 100 ul less concentrated formulation, and the 100 ul less concentrated formulation with Captique).

DESCRIPTION

Figure 2:
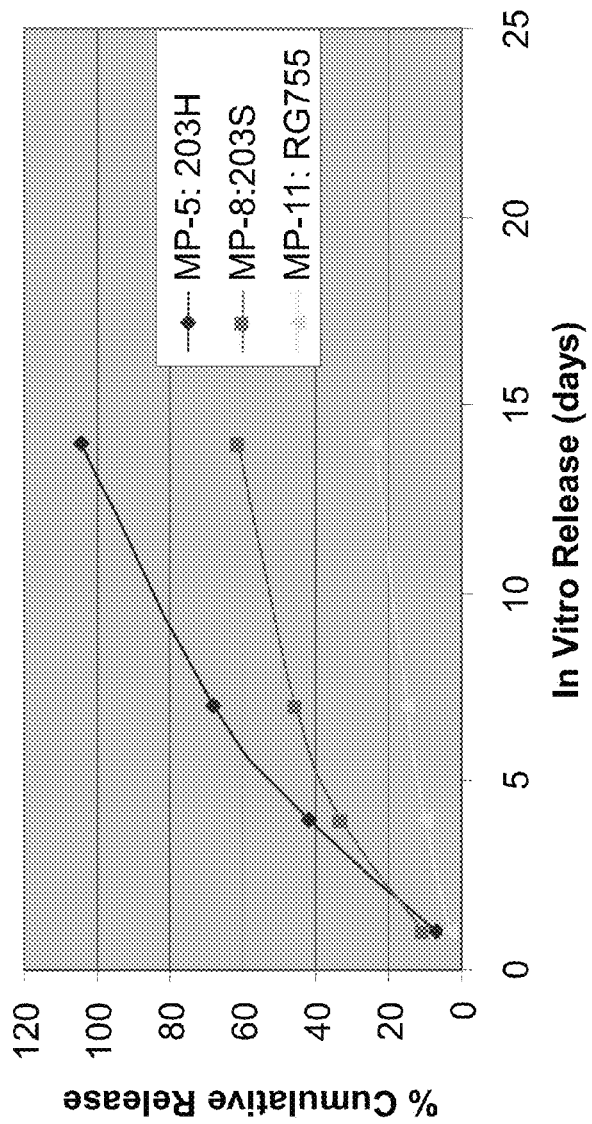
FIG. 2 is graph showing in vitro percent cumulative release of latanoprost from three samples of the FIG. 1 microspheres, over a 15 day period.

Our invention is based on the discovery of a novel pharmaceutical composition comprising latanoprost containing implants or microspheres and their effective use to treat glaucoma with (as compared to daily, topical Xalatan) reduced iris pigmentation, less hyperemia and many fewer required drug administrations (i.e. 3-8 times a year injection of latanoprost containing microspheres according to our invention as opposed to daily Xalatan eyedrops).

With the present latanoprost containing implant or microspheres the amount of the latanoprost released into the eye for a period of time greater than about one week after the implant or microparticles are placed in the eye is effective in treating or reducing a symptom of an ocular condition, such as ocular hypertension or a retinal degeneration disease or condition.

DEFINITIONS

The following definitions are used herein.

"About" means plus or minus ten percent of the number, parameter or characteristic so qualified.

"Microsphere" and "microparticle" are used synonymously to refer to a small diameter or dimension (see below) device or element that is structured, sized, or otherwise configured to be administered subconjunctivally (i.e. sub-tenon). Microspheres or microparticles includes particles, micro or nanospheres, small fragments, microparticles, nanoparticies, fine powders and the like comprising a biocompatible matrix encapsulating or incorporating a therapeutic agent. Microspheres are generally biocompatible with physiological conditions of an eye and do not cause significant adverse side effects. Microspheres administered subconjunctivally can be used safely without disrupting vision of the eye. Microspheres have a maximum dimension, such as diameter or length, less than 1 mm. For example, micrmarticles can have a maximum dimension less than about 500 µm. Microspheres can also have a maximum dimension no greater than about 200 µm, or may have a maximum dimension from about 30 µm to about 50 µm, among other sizes. An "implant" is a drug delivery device which is considerably larger than a microsphere, and whereas a plurality (i.e. hundreds or thousands)) of microspheres are administered to treat an ocular condition (such as glaucoma) usually only one to at most six implants are administered for the same purpose.

"Ocular region" or "ocular site" means any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

"Biodegradable polymer" means a polymer or polymers which degrade in vivo, and wherein erosion of the polymer or polymers over time occurs concurrent with or subsequent to release of the therapeutic agent. The terms "biodegradable" and "bioerodible" are equivalent and are used interchangeably herein. A biodegradable polymer may be a homopolymer, a copolymer, or a polymer comprising more than two different polymeric units. The polymer can be a gel or hydrogel type polymer, PLA or PLGA polymer or mixtures or derivatives thereof.

"Therapeutically effective amount" means level or amount of agent needed to treat an ocular condition, or reduce or prevent ocular injury or damage without causing significant negative or adverse side effects to the eye or a region of the eye. In view of the above, a therapeutically effective amount of a therapeutic agent, such as a latanoprost, is an amount that is effective in reducing at least one symptom of an ocular condition.

We have developed implants and microspheres which can release drug loads over various time periods. These implants or microspheres, which when inserted into the subconjunctival (such as a sub-tenon) space of an eye provide therapeutic levels of a prostamide or prostaglandin, such as latanoprost, for extended periods of time (e.g., for about 1 week or more). The disclosed implants and microspheres are effective in treating ocular conditions, such as ocular conditions associated with elevated intraocular pressure, and more specifically in reducing at least one symptom of glaucoma.

Additionally, we have developed novel methods for making implants and microspheres. The latanoprost of the present implants and microspheres is preferably from about 1% to 90% by weight of the microspheres. More preferably, the latanoprost is from about 5% to about 30% by weight of the implant or microspheres. In a preferred embodiment, the latanoprost comprises about 10% by weight of the microsphere (e.g., 5%-15%). In another embodiment, the latanoprost comprises about 40% by weight of the microspheres.

Suitable polymeric materials or compositions for use in the implant or microspheres include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present microspheres.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the selected therapeutic agent, ease of use of the polymer in making the drug delivery systems of the present invention, a half-life in the physiological environment of at least about 6 hours, preferably greater than about one day, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the microspheres. Different molecular weights of the same or different polymeric compositions may be included in the microspheres to modulate the release profile. For latanoprost implants, the relative average molecular weight of the polymer will preferably range from about 4 to about 25 kD, more preferably from about 5 to about 20 kD, and most preferably from about 5 to about 15 kD.

In some implants and microspheres, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the microspheres. The percentage of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the subconjunctival implants and microspheres may comprise a mixture of two or more biodegradable polymers. For example, the implants and microspheres may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implant or microspheres surface, dissolution, diffusion through porous channels of the hydrated polymer and erosion. Erosion can be bulk or surface or a combination of both. As discussed herein, the matrix of the microspheres may release drug at a rate effective to sustain release of an amount of the prostamide component for more than one week after implantation into an eye. In certain microspheres, therapeutic amounts of latanoprost are released for no more than about 3-30 days after administration to the subconjunctival space. For example, a microsphere may comprise latanoprost, and the matrix of the microsphere degrades at a rate effective to sustain release of a therapeutically effective amount of latanoprost for about one month after being placed under the conjunctiva. As another example, the microspheres may comprise latanoprost, and the matrix releases drug at a rate effective to sustain release of a therapeutically effective amount of latanoprost for more than thirty days, such as for about six months.

One example of the biodegradable implant or microsphere comprises latanoprost associated with a biodegradable polymer matrix, which comprises a mixture of different biodegradable polymers. At least one of the biodegradable polymers is a polylactide having a molecular weight of about 63.3 kD. second biodegradable polymer is a polylactide having a molecular weight of about 14 kD. Such a mixture is effective in sustaining release of a therapeutically effective amount of the latanoprost for a time period greater than about one month from the time the microspheres are placed administered under the conjuctiva.

Another example of a biodegradable implant or microsphere comprises latanoprost associated with a biodegradable polymer matrix, which comprises a mixture of different biodegradable polymers, each biodegradable polymer having an inherent viscosity from about 0.16 dl/g to about 1.0 dl/g. For example, one of the biodegradable polymers may have an inherent viscosity of about 0.3 dl/g. A second biodegradable polymer may have an inherent viscosity of about 1.0 dl/g. Additional microspheres may comprise biodegradable polymers that have an inherent viscosity between about 0.2 dl/g and 0.5 dl/g. The inherent viscosities identified above may be determined in 0.1% chloroform at 25° C.

The release of the latanoprost from an implant or microspheres into the subconjunctiva may include an initial burst of release followed by a gradual increase in the amount of the latanoprost released, or the release may include an initial delay in release of the prostamide component followed by an increase in release. When the microspheres are substantially completely degraded, the percent of the latanoprost that has been released is about one hundred. The implants and microspheres disclosed herein do not completely release, or release about 100% of the latanoprost, until after about one week of being placed in an eye.

It may be desirable to provide a relatively constant rate of release of the latanoprost from the microspheres over the life of the implanted or injected microspheres. For example, it may be desirable for the latanoprost to be released in amounts from about 0.01 µg to about 2 µg per day for the life of the microspheres. However, the release rate may change to either increase or decrease depending on the formulation of the biodegradable polymer matrix. In addition, the release profile of the prostamide component may include one or more linear portions and/or one or more non-linear portions. Preferably, the release rate is greater than zero once the microspheres has begun to degrade or erode.

The implants and microspheres can be monolithic, i.e. having the active agent or agents homogenously distributed through the polymeric matrix, or encapsulated, Where a reservoir of active agent is encapsulated by the polymeric matrix. Due to ease of manufacture, monolithic implants are usually preferred over encapsulated forms. However, the greater control afforded by the encapsulated microspheres may be of benefit in some circumstances, where the therapeutic level of the drug falls within a narrow window. In addition, the therapeutic component, including the latanoprost component, may be distributed in a non-homogenous pattern in the matrix. For example, the microspheres may include a portion that has a greater concentration of the latanoprost relative to a second portion of the microspheres.

The implants and microspheres disclosed herein may have a size of between about 5 µm and about 1 mm, or between about 10 µm and about 0.8 mm for administration with a needle. For needle-injected microspheres, the microsphere may have any appropriate dimensions so long as the longest dimension of the microsphere permits the microsphere to move through a needle. This is generally not a problem in the administration of microspheres. The subconjunctival space in humans is able to accommodate relatively large volumes of microspheres, for example, about 100 µl, or about 150 µl, or about 50-200 µl or more.

The total weight of implant or microsphere in a single dosage an optimal amount, depending on the volume of the subconjunctival space and the activity or solubility of the active agent. Most often, the dose is usually about 0.1 mg to about 200 mg of implant or microspheres per dose. For example, a single subconjunctival injection may contain about 1 mg, 3 mg, or about 5 mg, or about 8 mg, or about 10 mg, or about 100 mg or about 150 mg, or about 175 mg, or about 200 mg of microspheres, including the incorporated therapeutic component. For non-human individuals, the dimensions and total weight of the implant or microsphere(s) may be larger or smaller, depending on the type of individual.

The dosage of the therapeutic component (i.e. latanoprost) in the implant or microspheres is generally in the range from about 0.001% to about 100 mg per eye per dose, but also can vary from this depending upon the activity of the agent and its solubility.

Thus, implants or microspheres can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center of the microsphere may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implant or microspheres may be of any particulate geometry including micro and nanospheres, micro and nanoparticles, spheres, powders, fragments and the like. The upper limit for the microsphere size will be determined by factors such as toleration for the implant, size limitations on insertion, desired rate of release, ease of handling, etc. Spheres may be in the range of about 0.5 µm to 4 mm in diameter, with comparable volumes for other shaped particles.

The size and form of the implant or microspheres can also be used to control the rate of release, period of treatment, and drug concentration at the site of implantation. Larger microspheres will deliver a proportionately larger dose, but depending on the surface to mass ratio, may have a slower release rate. The particular size and geometry of the implant or microspheres are chosen to suit the activity of the active agent and the location of its target tissue.

The proportions of the latanoprost, polymer, and any other modifiers may be empirically determined by formulating several microsphere batches with varying average proportions. A USP approved method for dissolution or release test can be used to measure the rate of release (USP 23; NF 18 (1995) pp. 1790-1798). For example, using the infinite sink method, a weighed sample of the microspheres is added to a measured volume of a solution containing 0.9% NaCl in water, where the solution volume will be such that the drug concentration is after release is less than 5% of saturation. The mixture is maintained at 37° C. and stirred slowly to maintain the microspheres in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the latanoprost included in the implants and microspheres disclosed herein, the microsphere may also include one or more additional ophthalmically acceptable therapeutic agents. For example, the microspheres may include one or more antihistamines, one or more antibiotics, one or more beta blockers, one or more steroids, one or more antineoplastic agents, one or more immunosuppressive agents, one or more antiviral agents, one or more antioxidant agents, and mixtures thereof. Alternatively, a single injection of implant or microspheres can include two or more microsphere batches each containing a different therapeutic component or components. Such a mixture of different implants and microspheres in included within the present invention.

Additional pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loradatine, hydroxyzine, diphenhydramine, chlorpheniramine, brompheniramine, cyproheptadine, terfenadine, clemastine, triprolidine, carhinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Examples of beta blockers include acebutolol, atenolol, labetalol, metoprolol, propranolol, timolol, and derivatives thereof.

Examples of steroids include corticosteroids, such as cortisone, prednisolone, flurometholone, dexamethasone, medrysone, loteprednol, fluazacort, hydrocortisone, prednisone, betamethasone, prednisone, methylprednisolone, riamcinolone hexacatonide, paramethasone acetate, diflorasone, fluocinonide, fluocinolone, triamcinolone, derivatives thereof, and mixtures thereof.

Examples of antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamyl-cysteine, quercitin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha-2 adrenergic receptor agonists, antiparasitics, antifungals, and derivatives thereof.

The amount of active agent or agents employed in the microspheres, individually or in combination, will vary widely depending on the effective dosage required and the desired rate of release from the microspheres. Usually the agent will be at least about 1, more usually at least about 10 weight percent of the microsphere, and usually not more than about 80, more usually not more than about 40 weight percent of the microspheres.

Some of the present implants and microspheres can comprise a combination of two or more different latanoprost derivatives. One microsphere or dosage of microspheres may comprise a combination of bimatoprost and latanoprost. Another microsphere or dosage of microspheres may comprise a combination of bimatoprost and travoprost.

As discussed herein, the present implants and microspheres may comprise additional therapeutic agents. For example, one implant or microspheres dosage can comprise a combination of latanoprost and a beta-adrenergic receptor antagonist. More specifically, the microsphere or dosage of microspheres may comprise a combination of latanoprost and Timolol®. Or, a microsphere or dosage of microspheres may comprise a combination of latanoprost and a carbonic anyhdrase inhibitor. For example, the microsphere or dosage of microspheres may comprise a combination of latanoprost and dorzolamide (Trusopt®).

In addition to the therapeutic component, the implants and microspheres disclosed herein may include or may be provided in compositions that include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from about 0.001% to about 5% by weight, and preferably about 0.01% to about 2% by weight. In at least one of the present microspheres, a benzylalkonium chloride preservative is provided in the implant, such as when the latanoprost consists essentially of bimatoprost.

In some situations mixtures of implants and microspheres may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants or microspheres. The amount of release modulator employed will be dependent on the desired release profile, the activity of the modulator, and on the release profile of the latanoprost in the absence of modulator. Electrolytes such as sodium chloride and potassium chloride may also be included in the microspheres. Where the buffering agent or enhancer is hydrophilic, it may also act as a release accelerator. Hydrophilic additives act to increase the release rates through faster dissolution of the material surrounding the drug in the microspheres, which increases the surface area of the drug exposed, thereby increasing the rate of drug bioerosion. Similarly, a hydrophobic buffering agent or enhancer dissolves more slowly, slowing the exposure of drug, and thereby slowing the rate of drug bioerosion.

In certain microspheres, the combination of latanoprost and a biodegradable polymer matrix is released or delivered an amount of latanoprost between about 0.1 mg to about 0.5 mg for about 3-6 months after implantation or injection into the eye.

Various techniques may be employed to produce the implants and/or microspheres described herein. Useful techniques include, but are not necessarily limited to, self-emulsification methods, super critical fluid methods, solvent evaporation methods, phase separation methods, spray drying methods, grinding methods, interfacial methods, molding methods, injection molding methods, combinations thereof and the like.

As discussed herein, the polymeric component recited in the present method may comprise a biodegradable polymer or biodegradable copolymer. In at least one embodiment, the polymeric component comprises a poly (laotide-co-glycolide) PLGA copolymer. In a further embodiment, the PLGA copolymer has a lactide/glycolide ratio of 75/25. In a still further embodiment, the PLGA copolymer has at least one of a molecular weight of about 63 kilodaltons and an inherent viscosity of about 0.6 dL/g.

The present methods may also comprise a step of forming a first composition which comprises a latanoprost component, a polymeric component, and an organic solvent, and a step of forming a second oil-containing composition, and mixing the first composition and the second oil-containing composition.

In addition, the present population of microparticles may have a maximum particle diameter less than about 200 μm. In certain embodiments, the population of microparticles has an average or mean particle diameter less than about 50 μm. In further embodiments, the population of microparticles has a mean particle diameter from about 30 μm to about 50 μm.

The present implants and microparticles are structured or configured to release the latanoprost for extended periods of time at controlled rates. In some embodiments, the latanoprost is released at a substantially linear rate (e.g., a single rate) over the life of the microparticles (e.g., until the microparticles fully degrade). Other embodiments are capable of releasing the latanoprost at multiple rates or different rates over the life of the microparticles. The rate at which the microparticles degrade can vary, as discussed herein, and therefore, the present microparticles can release the latanoprost for different periods of time depending on the particular configuration and materials of the microparticles. In at least one embodiment, a microparticle can release about 1% of the latanoprost in the microparticles per day. In a further embodiment, the microparticles may have a release rate of about 0.7% per day when measured in vitro. Thus, over a period of about 40 days, about 30% of the latanoprost may have been released.

As discussed herein, the amount of the latanoprost present in the implants and microspheres can vary. In certain embodiments, about 10 wt % of the microspheres is the latanoprost. In further embodiments, the latanoprost constitutes about 5 wt % of the microspheres.

The microspheres, including the population of microspheres, of the present invention may be inserted into the subconjunctival (i.e. sub-tenon) space of an eye by a variety of methods. The method of placement may influence the therapeutic component or drug release kinetics. A preferred means of administration of the microspheres of the present invention is by subconjunctival injection. The location of the site of injection of the microspheres may influence the concentration gradients of therapeutic component or drug surrounding the element, and thus influence the delivery rate to a given tissue of the eye. For example, an injection into the conjunctiva toward the posterior of the eye will direct drug more efficiently to the tissues of the posterior segment, While a site of injection closer to the anterior of the eye (but avoiding the cornea) may direct drug more efficiently to the anterior segment.

Microparticles may be administered to patients by administering an ophthalmically acceptable composition which comprises the microparticles to the patient. For example, microparticles may be provided in a liquid composition, a suspension, an emulsion, and the like, and administered by injection or implantation into the subconjunctival space of the eye.

The present implants or microparticles are configured to release an amount of latanoprost effective to treat an ocular condition, such as by reducing at least one symptom of the ocular condition. More specifically, the microparticles may be used in a method to treat glaucoma, such as open angle glaucoma, ocular hypertension, chronic angle-closure glaucoma, with patent iridotomy, psuedoexfoliative glaucoma, and pigmentary glaucoma. By injecting the latanoprost component-containing microspheres into the subconjunctival space of an eye, it is believed that the latanoprost is effective to enhance aqueous humor flow thereby reducing intraocular pressure. Additionally, the present inventors have shown that subconjunctival delivery of microspheres containing latanoprost is able to provide quite high concentrations of the therapeutic agent to the retina of the eye.

The latanoprost containing implants and microspheres disclosed herein may also be configured to release the latanoprost with or without additional agents, as described above, which to prevent or treat diseases or conditions, such as the following: maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papiliophiebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

In one embodiment, an implant, such as the microspheres disclosed herein, is administered to a subconjunctival space of an eye. In at least one embodiment, a method of reducing intraocular pressure in an eye of a patient comprises administering a microsphere containing latanoprost, as disclosed herein, to a patient by subconjuctival injection. A syringe apparatus including an appropriately sized needle, for example, a 22 gauge needle, a 27 gauge needle or a 30 gauge needle, can be effectively used to inject the composition with into the subconjunctival space of an eye of a human or animal. Frequent repeat injections are often not necessary due to the extended release of the latanoprost from the microspheres.

In addition, for dual therapy approaches to treating an ocular condition, the method may include one or more additional steps of administering additional therapeutic agents to the eye, such as by topically administering compositions containing timolol, dorzolamide, and iatoprost, among others.

In another aspect of the invention, kits and packages treating an ocular condition of the eye are provided, comprising: a) a container comprising an extended release microsphere formulation comprising a therapeutic component including latanoprost, and a drug release sustaining component; and b) instructions for use. Instructions may include steps of how to handle the microspheres, how to insert the microspheres into an ocular region, and what to expect from using the microspheres.

In certain implants, the microspheres preparation comprises a therapeutic component which consists essentially of latanoprost, salts thereof, and mixtures thereof, and a biodegradable polymer matrix. The biodegradable polymer matrix may consist essentially of PLA, PLGA, or a combination thereof. When placed in the eye, the preparation releases about 40% to about 60% of the latanoprost to provide a loading dose of the latanoprost within about one day after subconjunctival administration. Subsequently, the microspheres release about 1% to about 2% of the latanoprost per day to provide a sustained therapeutic effect. Such implant or microsphere preparations can be effective in reducing and maintaining a reduced intraocular pressure, such as below about 15 mm Hg for several months, and potentially for one or two years.

Other microspheres disclosed herein may be configured such that the amount of the latanoprost that is released from the microspheres within two days of subconjunctival injection is less than about 95% of the total amount of the latanoprost in the microsphere. In certain formulations, 95% of the latanoprost is not released until after about one week of injection. In certain microsphere formulations, about 50% of the latanoprost is released within about one day of placement in the eye, and about 2% is released for about 1 month after being placed in the eye. In other microspheres, about 50% of the latanoprost is released within about one day of subconjunctival administration, and about 1% is released for about 2 months after such administration.

In an alternative embodiment, the present invention may comprise the installation of a hollow depot device, made from a biocompatible, preferably non-biodegradable, polymer in connection with and preferably penetrating the conjunctiva of an eye. Such a device is described, for example, in US Patent Publication 20050112175, hereby incorporated by reference herein. The depot is preferably refillable with microspheres comprising an ophthalmically active therapeutic component, such as an ophthalmically active latanoprost.

A pharmaceutical composition (such as an implant or microspheres) within the scope of our invention can be formulated with a high viscosity, polymeric gel to reduce dispersion of the composition upon intraocular injection. Preferably, the gel has a high shear characteristic, meaning that the gel can be injected into an intraocular site through a 25-30 gauge needle, and more preferably through a 27-30 gauge needle. A suitable gel for this purpose can be a hydrogel or a colloidal gel formed as a dispersion in water or other aqueous medium. Examples of suitable gels include synthetic polymers such as polyhydroxy ethyl methacrylate, and chemically or physically crosslinked polyvinyl alcohol, polyacrylamide, poly(N-vinyl pyrolidone), polyethylene oxide, and hydrolysed polyacrylonitrile. Examples of suitable hydrogels which are organic polymers include covalent or ionically crosslinked polysaccharide-based hydrogels such as the polyvalent metal salts of alginate, pectin, carboxymethyl cellulose, heparin, hyaluronate (i.e. polymeric hyaluronic acid) and hydrogels from chitin, chitosan, pullulan, gellan, xanthan and hydroxypropylmethylcellulose. Commercially available dermal fillers (such as Hylafrom®, Restylane®, Sculpture™ and Radiesse) can be used as the high viscosity gel in embodiments of our pharmaceutical composition.

Hyaluronic acid ("HA") is a polysaccharide made by various body tissues. U.S. Pat. No. 5,166,331 discusses purification of different fractions of hyaluronic acid for use as a substitute for intraocular fluids and as a topical ophthalmic drug carrier. Other U.S. patent applications which discuss ocular uses of hyaluronic acid include Ser. Nos. 11/859,627; 11/952,927; 10/966,764; 11/741,366; and 11/039,192 The pharmaceutical compositions within the scope of our invention preferably comprise a high viscosity hyaluronic acid with an average molecular weight between about 1 and 4 million Daltons, and more preferably with an average molecular weight between about 2 and 3 million Daltons, and most preferably with an average molecular weight of about (±10%) 2 million Daltons.

Dry uncrosslinked HA material comprises fibers or powder of commercially available HA, for example, fibers or powder of sodium hyaluronate (NaHA). The HA may be bacterial-sourced sodium hyaluronate, animal derived sodium hyaluronate or a combination thereof. In some embodiments, the dry HA material is a combination of raw materials including HA and at least one other polysaccharide, for example, glycosaminoglycan (GAG).

In our invention the HA used comprises or consists of high molecular weight HA. That is, nearly 100% of the HA material in the present compositions is a high molecular weight HA. High molecular weight HA means HA with a molecular weight of at least about 1.0 million. Daltons (mw$\geq 10^6$ Da) to about 4.0 million Da (mw$\leq 4\times 10^6$ Da), For example, the high molecular weight HA in the present compositions may have a molecular weight of about 2.0 million Da (mw $2\times 10^6$ Da). In another example, the high molecular weight HA may have a molecular weight of about 2.8 million Da (mw $2.8\times 10^6$ Da).

In an embodiment of our invention, dry or raw HA material (in this specific example, NaHA) having a desired high/low molecular weight ratio is cleaned and purified. These steps generally involved hydrating the dry HA fibers or powder in the desired high/low molecular weight ratio, for example, using pure water, and filtering the material to remove large foreign matters and/or other impurities. The filtered, hydrated material is then dried and purified. The high and low molecular weight NaHA may be cleaned and purified separately, or may be mixed together, for example, in the desired ratio, just prior to crosslinking.

At this stage in the process, the pure, dried NaHA fibers are hydrated in an alkaline solution to produce an uncrosslinked NaHA alkaline gel. Any suitable alkaline solution may be used to hydrate the NaHA in this step, for example, but not limited to an aqueous solution containing NaOH. The resulting alkaline gel will have a pH above 7.5, for example, a pH above 8, for example, a pH above 9, for example, a pH above 10, for example, a pH above 12, for example, a pH above 13.

In this specific example, the next step in the manufacturing process comprises the step of crosslinking the hydrated, alkaline NaHA gel with a suitable crosslinking agent, for example, BDDE.

The step of crosslinking may be carried out using means known to those of skill in the art. Those skilled in the art appreciate how to optimize the conditions of crosslinking according to the nature of the HA, and how to carry out the crosslinking to an optimized degree.

In some embodiments of the present invention, the degree of crosslinking is at least about 2% to about 20%, for example, is about 4% to about 12%, wherein the degree of crosslinking is defined as the percent weight ratio of the crosslinking agent to HA-monomeric units in the composition.

The hydrated crosslinked, HA gel may be neutralized by adding an aqueous solution containing HCl. The gel is then swelled in a phosphate buffered saline solution for a sufficient time and at a low temperature.

In certain embodiments, the resulting swollen gel (HA) is a cohesive gel having substantially no visible distinct particles, for example, substantially no visibly distinct particles when viewed with the naked eye. In some embodiments, the gel has substantially no visibly distinct particles under a magnification of less than 35×.

The gel ((HA) is now purified by conventional means for example, dialysis or alcohol precipitation, to recover the crosslinked material, to stabilize the pH of the material and remove any unreacted crosslinking agent. Additional water or slightly alkaline aqueous solution can be added to bring the concentration of the NaHA in the composition to a desired concentration. In some embodiments, the concentration of NaHA in the composition is in a range between about 10 mg/ml to about 30 mg/ml.

EXAMPLES

The following examples set forth specific, non-limiting embodiments of our invention Example 1

Method for Making Latanoprost Microspheres

Latanoprost containing microspheres were made by dissolving 20 mg of latanoprost and 100 mg polymer (Resomer 203H) in 0.8 ml ethyl acetate. A minimum amount of dichloromethane was added to complete dissolution. Then added to this solution was 40 ml 1% polyvinyl acetate in water via a micro-pipette while shearing the mixture at 3000 rpm for 5 minutes with a Silverson homogenizer. When the polymer solution was added to the water, the pipette tip was submerged under the water surface and added dropwise.

After shearing, a milky white emulsion was formed, and it was mildly agitated in a hood for 3-5 hrs to allow solvent evaporation. This suspension was filtered through a 106 um sieves, and particle size was measured. The suspension was then centrifuged at 2000 rpm for 15 min to remove supernatant, followed by adding 10 mL distilled water to reconstitute the microspheres. Finally the microspheres were lyophilized followed by drug content assay, and in vitro release assay. Typical microsphere diameters were about 35 um, with 13% latanoprost loading.

Samples of the microspheres were formulated with a high viscosity hyaluronic acid. Thus, 10 mg microspheres were mixed with 100 uL Captique gel and another 10 mg microsphere sample was mixed with 50 uL J18 gel.

FIG. 1 provides information regarding sixteen batches of latanoprost microspheres made using various known bio-erodible polymers, such as R203H and RG502H. First day in vitro release (in PBS medium with 0.1% triton 100) rates varied from 3% to 60% of the latanoprost, and microsphere mean diameter ("PS", i.e. particle size in FIG. 1) was between 18 and 52 microns. In FIG. 1 "d10" is the mean particle size possessed by 10% or less of the total number of microspheres made in that batch, while d90 is the mean particle size possessed by 90% or less of the total number of microspheres made in that batch. FIG. 2 shows in vitro release of latanoprost from selected microsphere formulations over a 15 day period.

Example 2

In Vivo Use of Latanoprost Microspheres to Lower Intraocular Pressure

Experiments were carried out in which the latanoprost containing microspheres of Example 1 were administered by subtenon injections in dogs. Intraocular pressure (IOP) and eye surface hyperemia were followed for a month after injection. It was observed that a concentrated microsphere formulation provided longer IOP lowering effects.

Latanoprost containing microspheres injected were formulated with and without a HA (Captique or J18, both being partially cross-linked HAs).

The methods for injecting the dogs was as follows:
1. Baseline examination procedures were as follows for Beagle dogs. Both eyes prior to application of test material had:
   a. Recorded gross ocular features
   b. External photographs were taken
   c. IOP was measured
   d. Pupil diameter (mm) was measured.
2. Sedation was performed using an IV injection of Propofol and a SQ injection atropine as a pre-anesthetic.
3. After sedation, proparacaine and betadine ophthalmic solution were applied.
4. The injection was given through a 25 G gauge needle into the superior temporal sub-tenon space.
5. Ocuflox ophthalmic solution was applied BID for two days.
6. Follow-up examinations was performed using the procedures in step 1.
7. Follow-up schedule: Day 1, Day 2, Week 1, Week 2, Week 3, and Week 4.

Results: FIG. 3 shows the concentration of the latanoprost containing microspheres used with and without hyaluronic acid (Captique). The use of a more concentrated suspension of latanoprost containing microspheres (i.e. the 50 ul formulation) and the use of the latanoprost containing microspheres in Captique permitted localization of the latanoprost containing microspheres in the episclera and also prevented excessive dispersion of the microspheres in the sub-Tenon's space. Thus we found that the 100 ul (less concentrated formulation) microsphere injection would readily disperse 180 degrees around the eye. Surprisingly, as shown by FIG. 3 some of the formulations reduced the TOP more than Xalatan® eye drops in the same dogs. IOP reduction by Xalatan® eye drop is shown by the "Max Topical Decrease" data point in FIG. 3. In FIG. 3 the "50 ul" formulation consisted of 20 weight % latanoprost containing microspheres (total of 1240 ug latanoprost in the microspheres present in the 50 ul suspension) and 80 weight % liquid vehicle (2% carboxymethylcellulose with 0.1% tween 80 in saline). The "100 ul" formulation consisted of 10 weight % latanoprost containing microspheres (total of 1240 ug latanoprost in the microspheres present in the 100 ul suspension) and 90 weight % of the same liquid vehicle (2% CMC, 0.1% tween 80 in saline). Finally in FIG. 3 the "100 ul w/Captique" formulation consisted of 10 weight % latanoprost containing microspheres (total of 1240 ug latanoprost in the microspheres present in the 100 ul suspension) and 90 weight % Captique gel (HA).

The results of using a higher concentration of latanoprost containing microspheres and also the use of an HA with the latanoprost containing microspheres was found to lower the IOP more efficiently and also provided less conjunctival hyperemia. This may be the result because if drug dispersion is reduced, then there is less conjunctiva that has exposure to the microspheres and thereby less clock hours of conjunctiva that show hyperemia.

Figure 5:
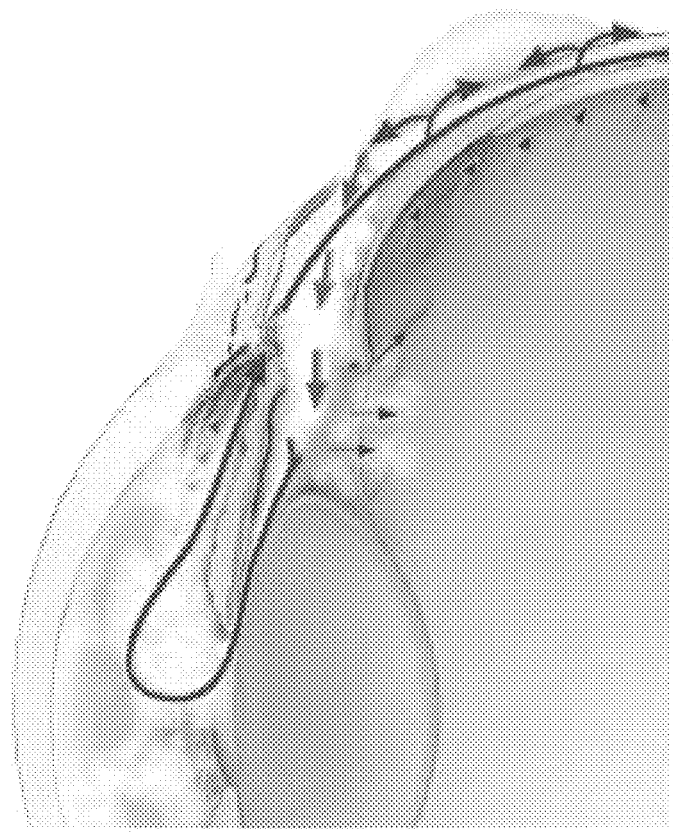
FIG. 5 is cross sectional view of a diagramatic representation of the same portion of a human eye shown in FIG. 4 with the arrows now showing that the flow of aqueous humor away from the ciliary body carries substantial amounts of anterior sub-tenon injected away from the site o injection into the anterior chamber of the eye.
Figure 4:
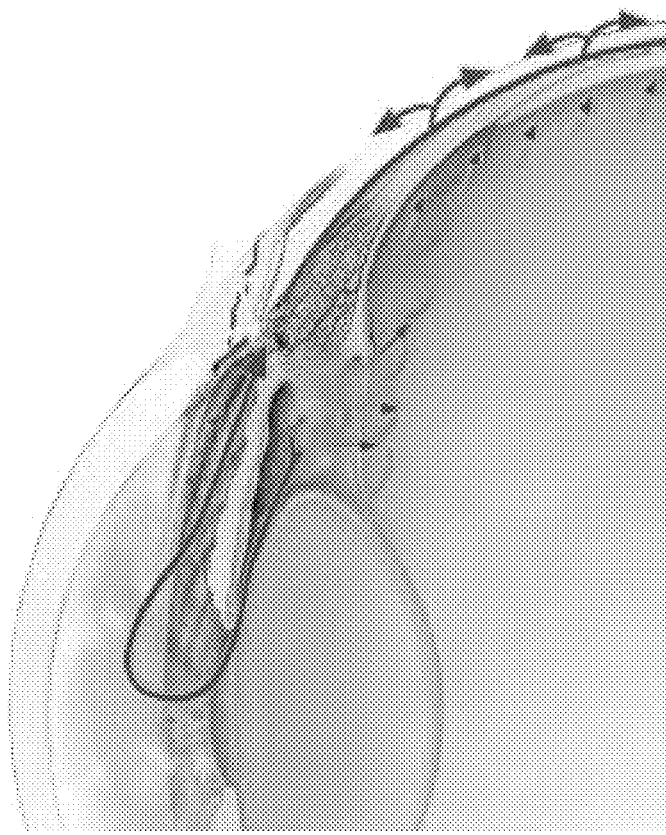
FIG. 4 is a cross sectional view of a diagramatic representation of a portion of a human eye showing (the arrows) the direction of flow of aqueous humor made by the ciliary body away from the ciliary body.

An "anterior" intraocular location for the purpose of this Example means a sub-Tenon, subchoroidal, suprachoroidal, intrascleral, episcleral, and the like intraocular location which is located no more than about 10 mm (and preferably no more than about 8 mm and more preferably less than about 5-6 mm) along the curvature of the surface of the eye from the corneal limbus. On the other hand a "posterior" intraocular location for the purpose of this Example means into a location behind the equator of the eye, that is a location at least about 8-9 mm or more away from the limbus. We compared injection of latanoprost containing microspheres in the "anterior" vs "posterior" (as respectively defined above in this Example) sub-Tenon space of the eye. We determined that an anterior injection location is preferred because that placed the microspheres in the juxtascleral area adjacent to the ciliary body at what we call "the anterior portal". Without wishing to be bound by theory we can propose an explanation as to why anterior sub-tenon injection of latanoprost containing microspheres can provide a greater (more IOP lowering) and/or a longer lasting IOP lowering effect. Thus, as shown by FIG. 4 aqueous humor (AH) production occurs via ultrafiltration at the ciliary body (blue in FIG. 4 represents the ultrafiltrate fluid). The pathway of the fluid produced at the ciliary body is illustrated by the arrows, some enter the posterior chamber (area behind the iris), and then the fluid percolates through the pupil and eventually into the trabecular meshwork. Other fluid goes into the vitreous humor and the net fluid movement is outward due to 1)hydrostatic Pressure and 2) osmotic pressure gradients in areas posterior to pars plicata region. Therefore, fluid movement in the vitreous posterior to the pars plicata region is counter-directional to inward diffusion drug placed in the sub-Tenons (episcleral) space. FIG. 5 shows that drug (white color) such as latanoprost that is diffusing is actually facilitated when diffusing from the anterior sub-Tenon area to the anterior chamber since the net fluid movement is inward in this area. More posterior, the net fluid movement is outward and no drug (i.e. latanoprost) is shown diffusing into the vitreous. Hence we determined that a facilitated pathway into the eye exists and we cal it the "anterior portal pathway".

To test the hypothesis of the anterior portal, and therefore the existence of a preferred sub-tenon injection location (at the anterior sub-Tenon so as to access the area to access the anterior pathway portal), we injected latanoprost containing microspheres both sub-tenon anteriorly or posteriorly. Significantly, the posterior injection showed no IOP reduction. The anterior sub-tenon injection of latanoprost containing microspheres with or without a high viscosity hyaluronic acid did show IOP reduction. Importantly, the microsphere-J18 formulation maintained intraocular residency of the microspheres longer than did neat (in saline, no HA) injections of the microspheres.

We found that in vivo (sub-tenon in dogs) administration of latanoprost containing microspheres formulated with a high viscosity hyaluronic acid provided a greater decrease of baseline IOP than did the same latanoprost containing microspheres not formulated with a high viscosity hyaluronic acid. See eg FIG. 3. Captique (available from Allergan, Irvine, Calif. or from Genzyme Corp, Cambridge, Mass.) is a cross linked hyaluron (hyaluronic acid) with an average molecular weight of about 2 million Daltons. Similar results (greater change from IOP baseline upon sub-tenon administration in dogs) were obtained when the microspheres MP5 (total of 1242 micro grams of latanoprost contained by the sample of MP5 used) were formulated with 50 micro liters of another high viscosity hyaluronic acid J18 (J18 is Juvederm 18, available from Allergan, Irvine, Calif. J18 is a cross linked (less than 6% cross linked) hyaluronic acid (18 mg in 1 ml of phosphate butter pH 7.2) with an average molecular weight of about 2 million Daltons, and a G' value of about 60.

It was surprizing and unexpected to observe that latanoprost containing microspheres upon intraocular administration provide a greater decrease from baseline IOP when formulated with a high viscosity hyaluronic acid. It can be inferred therefore that in some way the presence of a high viscosity hyaluronic acid in the formulation (as a carrier for the latanoprost containing microspheres) potentates or increases the IOP lowering effect of the latanoprost released from the microspheres. Additionally, ophthalmologists are adverse to injecting a bioerodible polymer drug delivery device (such as a composition within the scope of the present invention into an anterior sub-tenon because of the widely held belief they have that any polymer remnant will remain visible long after injection, thereby providing a cosmetic deterrent to treatment by such an administration route. Contrary to this widely held belief we determined that anterior sub-tenon injection of latanoprost containing microspheres does not result at any time in a visible remnant.

The benefits of using microsphere in gel (high viscosity hyaluronic acid) formulation include that ease of the injection was significantly improved when comparing with suspension (no HA) formulation (no syringe clogging upon injection); storage stability (no microsphere settling upon storage of the formulation), and formation of a concise and maintained depot at the site of intraocular injection.

Example 3

Subconjunctivally Injected Latanoprost Microspheres to Treat Glaucoma

A 56 year old male suffering from glaucoma in both eyes receives a subconjunctival injection of PLGA microspheres containing latanoprost (as set forth in Example 2) made by the method of Example 1 within the anterior sub-tenon space of each eye. The microspheres contain 10 weight % latanoprost, and 20 mg of microspheres are used for each injection. In about two days, the patient reports a substantial relief in ocular comfort. Determination, of intraocular pressure (IOP) reveals that the IOP has decreased in each eye, the average intraocular pressure measured at 8:00 AM has decreased from 28 mm Hg to 14.3 mm Hg. The patient is monitored every other day for about 1 month. Intraocular pressure levels remain below 15 mm Hg for this period of time, and the patient reports reduced ocular discomfort. Little or no ocular hyperemia is observed and no iris color or pigmentation change is observed. Furthermore, the microspheres nor any portion thereof cannot be seen at any time after injection when the patient is observed facing the observing at a distance of 3 feet or more with normal eye activity, without the eyelids being depressed or the conjunctiva exposed for examination. In other words there was no cosmetic effect on any aspect of the patient's appearance from the sub-tenon injection of the latanoprost containing microspheres.

Example 4

Method for Making Latanoprost Implants

Latanoprost is a prostaglandin $F_{2\alpha}$ analogue approved for treatment of open-angle glaucoma or ocular hypertension in patients who are intolerant of other intraocular pressure lowering medications or insufficiently responsive (i.e. failed to achieve target IOP after multiple measurements over time) to another IOP-lowering medication. Latanoprost may be used alone or in combination with other antiglaucoma agents. Latanoprost is an isopropyl ester prodrug. It is hydrolyzed by esterases in the cornea to latanoprost acid, which is biologically active. The elimination of latanoprost acid from plasma is rapid (half-life 17 minutes) after either ophthalmic or intravenous administration. Thus, there is a need for a latanoprost sustained release polymer implant, which can be uses as an effective treatment for long-term reduction of intraocular pressure associated with glaucoma or other ocular diseases. In this Example we made sustained, release polymeric implants containing therapeutically effective amounts of latanoprost.

Latanoprost (molecular weight 432.58 and approximate pH 6.7) is a colorless to slightly yellow oil that is very soluble in acetonitrile and freely soluble in acetone, ethanol, ethyl acetate, isopropanol, methanol and octanol. It is practically insoluble in water.

Implants were made by hot-melt extrusion to contain 30 wt % latanoprost, 40-60 wt % of a biodegradable poly (D,L-lactide-co-glycolide) polymer (Resomer® RG752s) (PLGA), 0-20% of a biodegradable poly (D,L-lactide) polymer (Resomer® R202s)(PLA), and 10% PEG-3350. The formulations and in vitro drug release profile for the two implants made are summarized in Table 1 and FIG. 6, respectively.

TABLE 1

Latanoprost containing Implants

Weight %

| Formulation No. | Latanoprost | Resomer RG752s | Resomer R202s | PEG-3350 |
|---|---|---|---|---|
| 8933-070 | 30 | 60 | 0 | 10 |
| 28933-085 | 30 | 40 | 20 | 10 |

Manufacturing Method (Low Temperature Extrusion)

The latanoprost containing bioerodible polymer implants in this Example were made by hot-melt extrusion using a mechanically driven ram microextruder but they can also be made by direct compression or solvent casting. The implants were rod-shaped, but they can be made into any geometric shape by changing the extrusion or compression die. Polymers (the (resomers) were used as received from Boehringer Ingelheim and latanoprost was used as received from Daiichi Fine Chemical Co., Ltd.

The samples were initially mixed (including the resomer powder and the 10 weight % PEG) using a spatula in a weigh-boat for 15 minutes. The samples were then transferred into a stainless steel container containing two ¼" stainless steel ball and mixing continued using a Turbula mixer for two separate 15 minute cycles. The powder blend was mixed by hand using a spatula between each cycle and after the final cycle. The blended material was then compacted into an extruder barrel and the extruder barrel was placed into the heated well (between 50 and 55 degrees C.) of the piston extruder and extruded using 500 pm nozzle and a speed setting number of 0.0025.

We developed this low temperature extrusion method because latanoprost is an oil at room temperature and begins to lose biological activity if headed above about 56° C. A low temperature extrusion is possible due to use of about 5-10 weight % PEG as a co-solvent for the resomers. Other suitable PEGS which can be used in this method are PEG 5000 and PEG 7000. Up to about PEG10,000 is suitable. Besides a PEG other suitable co-solvents include 5-10 weight % cholesterol and polyvinylprovidine. See eg U.S. patent application Ser. No. 11/612,928, filed Dec. 19, 2006. The method disclosed herein permitted extrusion at a temperature even lower than that disclosed in application Ser. No. 11/612,928. Preferably the resomers used have a relatively low molecular weight so as to form implants which homogenously incorporate biologically active latanoprost, and so that the implant do not have significant burst release of drug upon intraocular administration. Thus the RG752s resomer has an inherent viscosity of from 0.16 to 0.024 dl/g and R202s resomer has an inherent viscosity of 0.2 dl/g and these resomers have average molecular weights of about 11,200 and 6,500, respectively.

Figure 6:
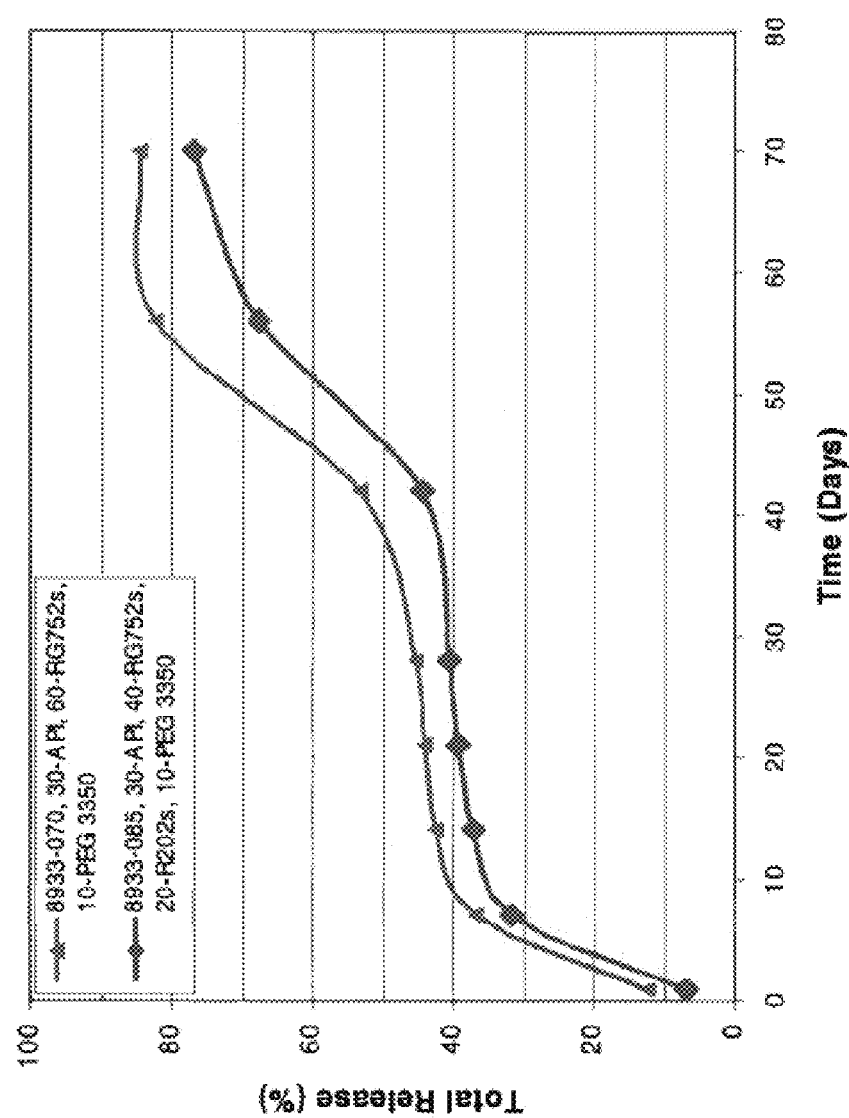
FIG. 6 is a graph showing in vitro release over a 70 day period of latanoprost from the implants made in Example 4.

The extruded filaments were cut into one milligram implant (approximately 3 mm long), and (for in vitro release study) placed into a 10 ml vial containing 0.01 M phosphate buffered saline (pH 7.4), and then transferred into a shaking water bath set at 37° C. and 50 rpm. At various time points, the solution was removed and analyzed by HPLC to determine the amount of latanoprost released by the implants. The removed solution was replaced with fresh phosphate buffered saline solution. The release profiles observed are shown by FIG. 6.

Example 5

Subconjunctivally Injected Latanoprost Implant to Treat Glaucoma

A 64 year old female suffering from glaucoma in both eyes receives subconjunctival administration of a PLGA/PLA implant containing latanoprost made by the method of Example 4 within the anterior sub-tenon space of each eye. The implant contains 30 weight % latanoprost. In about two days, the patient reports a substantial relief in ocular comfort. Determination of intraocular pressure (IOP) reveals that the Iop has decreased in each eye, the average intraocular pressure measured at 8:00 AM has decreased from 28 mm Hg to 14.3 mm Hg. The patient is monitored every other day for about 1 month. Intraocular pressure levels remain below 15 mm Hg for this period of time. Little or no ocular hyperemia is observed and no iris color changes is observed.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A method of treating glaucoma, the method comprising anterior sub-tenon administration to a patient with glaucoma of a 50-µl pharmaceutical composition consisting of:
    (a) a plurality of microspheres made from a PLGA and/or PLA;
    (b) 1242 micrograms of latanoprost contained by the microspheres, and;
    (c) 50 µl of a high viscosity hyaluronic acid, the high viscosity hyaluronic acid corresponding to a gel formed of 18 mg of a cross-linked hyaluronic acid in 1 ml of phosphate buffer at pH 7.2, the cross-linked hyaluronic acid having an average molecular weight of about 2 million Daltons, thereby treating the glaucoma.

* * * * *